United States Patent [19]
Davis et al.

[11] 4,131,624
[45] Dec. 26, 1978

[54] REDUCTION OF PHOSPHINE OXIDES
[75] Inventors: William R. Davis, South Plainfield; Michael D. Gordon, Clark, both of N.J.
[73] Assignee: M&T Chemicals Inc., Stamford, Conn.
[21] Appl. No.: 812,761
[22] Filed: Jul. 5, 1977
[51] Int. Cl.$^2$ .............................................. C07F 9/50
[52] U.S. Cl. ............................................ 260/606.5 P
[58] Field of Search .................................. 260/606.5 P

[56] References Cited
U.S. PATENT DOCUMENTS

| | | | |
|---|---|---|---|
| 3,261,871 | 7/1966 | Fritzsche et al. | 260/606.5 P |
| 3,280,195 | 10/1966 | Fritzsche et al. | 260/606.5 P |
| 4,008,282 | 2/1977 | Townsend et al. | 260/606.5 P |

OTHER PUBLICATIONS

"Preparative Inorganic Reactions", vol. 2, Chapt. 2, p. 93, Wiley-Interscience, N. Y. 1965.
Fessenden et al., Chemical Reviews, 61, 361 (1971).
Speier et al., J.A.C.S. 79 974 (1957).
Speier et al., J. Org. Chem. 35 3879 (1970).
Bailar, The Chemistry of the Coordination Compounds, Reinhold Publ. Corp., N. Y., p. 129 (1956).
Kasolapoff et al., Organic Phosphorus Compounds, Wiley-Interscience, N. Y., pp. 45-47 (1972).
Fritzsche et al., Ber. 97 1988-1993 (1964).
Naumann et al., J.A.C.S. 91 (25) 7012-7023 (1969).

Primary Examiner—Helen M. S. Sneed
Attorney, Agent, or Firm—Kenneth G. Wheeless; Robert Spector

[57] ABSTRACT

Tertiary phosphine oxides are reduced to the corresponding phosphines by halosilanes in the presence of a stoichiometric amount of a primary or secondary amine. The reduction in yield expected using a primary or secondary amine in place of the prior art tertiary amine is not observed.

8 Claims, No Drawings

REDUCTION OF PHOSPHINE OXIDES

BACKGROUND OF THE INVENTION

This invention relates to a method for preparing tertiary phosphines from the corresponding phosphine oxide. More specifically, this invention relates to the reduction of tertiary phosphine oxide using halosilanes under conditions considered undesirable by the prior art.

The prior art teaches the reduction of tertiary phosphine oxides by halosilanes in the presence of tertiary amines. Specifically, U.S. Pat. No. 3,261,871 discloses that a tertiary phosphine oxide can be reduced by reacting from 0.7 to 1.5 moles of a halosilane containing the residue

and from 0.7 to 1.5 moles of a tertiary amine for each mole of the tertiary phosphine oxide. This patent teaches that the amine is employed to react with the hydrogen halide formed as a by-product during the reaction. Primary and secondary amines are known to displace halogen atoms bonded directly to silicon to form aminosilanes. In accordance with this teaching of the aforementioned U.S. Pat. No. 3,261,871, primary and secondary amines would be unsatisfactory acid acceptors since the one or two hydrogen atoms bonded to the nitrogen of the amine are sufficiently reactive to displace halogen as a hydrogen halide from the silane reagent and form an aminosilane which may not be capable of reducing the phosphine oxide.

An objective of this invention is to provide a method for increasing the yield and purity of tertiary phosphines formed by reacting the corresponding phosphine oxide with a halosilane. It has now been found that this objective can be achieved if the reaction is carried out in the presence of at least a stoichiometric amount of a primary or secondary amine, which is contrary to the teaching of the prior art.

SUMMARY OF THE INVENTION

This invention provides an improved method for preparing tertiary phosphines by reacting the corresponding phosphine oxide with a halosilane containing the residue

wherein X is halogen, in the presence of an amine. The improvement resides in employing a primary or secondary amine in a stoichiometric amount, based on the number of moles of tertiary phosphine oxide. Contrary to what one would expect from the prior art, the yield of phosphine is actually increased rather than decreased as a result of a reaction between the silane and the amine.

DETAILED DESCRIPTION OF THE INVENTION

The inorganic and organic silicon compounds which can be reacted with a tertiary phosphine oxide in accordance with the present method are described in the aforementioned U.S. Pat. No. 3,261,871, the pertinent sections of which are hereby incorporated by reference. Useful silicon compounds include silanes containing a hydrogen and at least one halogen atom bonded to silicon. The halogen is preferably chlorine or bromine. The other two groups bonded to the silicon atom are not critical to the operability of the present method. The remaining two groups can be monomeric or polymeric. Suitable monomeric groups are aromatic or aliphatic hydrocarbyl that may contain one or more heteroatoms such as oxygen, sulfur or nitrogen, alkoxy, hydrogen or halogen. Representative classes of useful silanes include the hydrocarbylhalosilanes such as phenydichlorosilane, hydrocarbyloxyhalosilanes such as ethoxydichlorosilane, and unsubstituted halosilanes such as chlorosilane and dichlorosilane. An especially preferred silane is trichlorosilane.

The amines employed in the present method are represented by the general formula $R_nNH_{3-n}$ wherein n is 1 or 2 and R is alkyl containing from 1 to 20 carbon atoms, cycloalkyl, aryl, alkaryl or aralkyl. Preferably R is alkyl and contains from 4 to 12 carbon atoms. When two R groups are present these can be the same or different. The R groups may contain substituents which will not interfere with the reaction of the phosphine oxide. Representative substituents include amido, alkoxy, alkylthio, keto

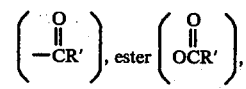

cyano (C≡N), nitro (—NO$_2$) and halogen groups. R' is selected from the same group as R.

Alternatively the amine may contain 2 or more basic nitrogen atoms, such as triethylene diamine, or it may be a polymer wherein the repeating units contain amine groups, such as poly(p-aminostyrene).

The number of moles of amine groups present is at least stoichiometrically equal to the number of moles of silane present in the reaction mixture. While not wishing to be bound by any theory, it appears as if the amine is reacting with the silane to form an amine-substituted silane that subsequently reacts with the tertiary phosphine oxide. The amine is recovered when the reaction product is hydrolyzed using an aqueous solution containing an alkali metal or alkaline earth metal hydroxide.

The phosphine oxides that can be reduced according to the present method contain three hydrocarbon groups bonded to the phosphorus atom by means of carbon-phosphorus bonds. Each of the hydrocarbon groups, which may or may not be identical, contain from 1 to 20 carbon atoms. Alternatively, one of the hydrocarbon groups can be part of a polymer chain, such as a phenyl group on a polystyrene molecule. These groups can be alkyl, cycloalkyl, aryl or alkaryl. The present method is particularly useful for reducing triaryl phosphine oxides such as triphenyl phosphine oxide. As previously disclosed for the amine, the hydrocarbon groups may contain substituents which will not interfere with the reduction of the phosphine oxide. Representative substituents include amido, alkoxy, alkylthio, keto

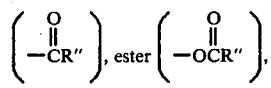

cyano (—C≡N), nitro (—NO₂) and halogen groups. R" is selected from the same group as R and R'".

The reaction between the phosphine oxide, silane and amine is preferably conducted at elevated temperatures. If the silane is trichlorosilane the preferred temperature range is usually from 50 to about 130° C. and the reaction is substantially complete in from 30 minutes to 5 hours. Preferably all of the amine is present throughout the reaction, although this may not be necessary. The amine may be added gradually as the reaction progresses.

A solvent is not mandatory, but the inclusion of inert organic solvents such as ethers may under certain circumstances be desirable and even produce a greater yield of phosphine and minimize the decomposition of the phosphine oxide to other products. For example, excellent results are obtained with such materials as benzene, toluene, diethylene glycol dimethyl ether, diethylene glycol diethyl ether, and diphenyl oxide. Although the amount of solvent is not in any way critical, from about 0.5 to 4 parts by weight for every part by weight of phosphine oxide is suitable with equal parts by weight usually preferred.

At the completion of the reaction process and prior to the isolation of the desired phosphine, the reaction mass is usually treated with alkali, such as caustic soda solution, calcium hydroxide or sodium carbonate. Conveniently, the reaction mixture may be added to a 10 to 20% excess of aqueous alkali and the resulting organic and aqueous phases separated. The phosphine product may be obtained from the separated organic phase by any convenient method, such as distillation, crystallization, adduct formation and precipitation, and the like. If desired, the amine reagent may be recovered for reuse. Distillation or extraction with aqueous acid solution of the aforementioned organic phase prior to isolation of phosphine removes the amine.

The following specific examples of the invention will serve to illustrate more clearly the application of the present method without limiting the scope of the accompanying claims.

EXAMPLE

A reactor equipped with an agitator, addition funnel, reflux condenser, heating means, and nitrogen blanket was charged with 208.7 g. (0.75 mole) of triphenylphosphine oxide, 146.4 g. (0.79 mole) of di-n-hexylamine, and 680 g. of toluene.

To the stirred reaction mixture was added dropwise 107.0 g. (0.79 mole) of trichlorosilane over 30 minutes as the temperature of the mixture increased to ambient to a maximum of 45° C. The mixture was then heated to the boiling point (105± 3° C.) and held there for 2.5 hours. The white reaction mixture was cooled to room temperature and hydrolyzed by gradually transferring it to a 5 liter flask containing a solution prepared using 139 g. of sodium hydroxide and 425 g. of water. The resultant mixture was stirred for 30 minutes, at which time the aqueous silicate layer was separated. The solid material remaining at the bottom of the organic phase was removed by washing with a solution containing 50 g. of sodium hydroxide and 150 g. of water. The organic layer was dried by azeotropic distillation and then filtered. The toluene was removed by distillation at atmospheric pressure, at which time the pressure was reduced to 10 mm. Hg. Following a small forerun, 125.6 g. (83% recovery) of di-n-hexylamine was distilled at 109–111° C. The residue in the reactor consisted of crude triphenylphosphine, and weighed 185.5 g. (94.3% yield).

Analysis by two separate methods (gas chromotography and potentiometric titration) showed the residue to consist of 95.7% triphenylphosphine. The remaining 4.3% was amine and unreacted triphenylphosphine oxide.

The yield of pure triphenylphosphine was 90.2%, based on triphenylphosphine oxide.

The foregoing procedure was repeated using n-butylamine in place of the di-n-hexylamine. The yield and purity of the final product were 96.4% and 95.8%, respectively.

What is claimed is:

1. In an improved method for converting a tertiary phosphine oxide to the corresponding tertiary phosphine by reacting the phosphine oxide with a silicon compound containing the structure

wherein X is halogen, in the presence of a stoichiometric amount of an amine, the improvement which consists of selecting the amine from the group consisting of monofunctional and polyfunctional primary and secondary amines.

2. An improved method according to claim 1 wherein the tertiary phosphine oxide is a triarylphosphine oxide.

3. An improved method according to claim 2 wherein the triarylphosphine oxide is triphenylphosphine oxide.

4. An improved method according to claim 1 wherein the silicon compound is a trihalosilane.

5. An improved method according to claim 4 wherein the trihalosilane is trichlorosilane.

6. An improved method according to claim 1 wherein the amine is a monofunctional primary amine.

7. An improved method according to claim 1 wherein the amine is a monofunctional secondary amine.

8. An improved method according to claim 1 wherein all of said amine is present throughout the entire reaction of said phosphine oxide with said silicon compound.